(12) United States Patent
Minowa et al.

(10) Patent No.: US 8,017,797 B2
(45) Date of Patent: Sep. 13, 2011

(54) METHOD FOR PRODUCING PHOSPHORUS-CONTAINING α-KETO ACID

(75) Inventors: Nobuto Minowa, Kanagawa (JP);
Nozomu Nakanishi, Kanagawa (JP);
Masaaki Mitomi, Kanagawa (JP)

(73) Assignee: Meiji Seika Kaisha Ltd., Tokyo (JP)

( * ) Notice: Subject to any disclaimer, the term of this patent is extended or adjusted under 35 U.S.C. 154(b) by 202 days.

(21) Appl. No.: 12/530,022

(22) PCT Filed: Mar. 21, 2008

(86) PCT No.: PCT/JP2008/055206
§ 371 (c)(1),
(2), (4) Date: Sep. 4, 2009

(87) PCT Pub. No.: WO2008/117733
PCT Pub. Date: Oct. 2, 2008

(65) Prior Publication Data
US 2010/0063313 A1    Mar. 11, 2010

(30) Foreign Application Priority Data

Mar. 23, 2007 (JP) ................................. 2007-076541

(51) Int. Cl.
*C07C 67/00* (2006.01)
(52) U.S. Cl. ............... 560/51; 560/76; 560/78; 560/81; 560/103; 560/106; 560/109; 560/130; 560/146; 560/174; 560/176; 560/190; 560/191
(58) Field of Classification Search .................. 560/51, 560/76, 78, 81, 103, 106, 109, 130, 146, 560/174, 176, 190, 191
See application file for complete search history.

(56) References Cited

U.S. PATENT DOCUMENTS

| | | |
|---|---|---|
| 4,399,287 A | 8/1983 | Baillie et al. |
| 6,936,444 B1 | 8/2005 | Bartsch |
| 2008/0146837 A1 | 6/2008 | Minowa et al. |
| 2009/0270647 A1 | 10/2009 | Minowa et al. |

FOREIGN PATENT DOCUMENTS

| | | |
|---|---|---|
| EP | 0121226 | 10/1984 |
| EP | 0249188 | 12/1987 |
| JP | 56-092897 | 7/1981 |
| JP | 59-184196 | 10/1984 |
| JP | 64-27485 | 1/1989 |
| JP | 5-247068 | 9/1993 |
| JP | 2003-528572 | 9/2003 |
| JP | 2004-245963 | 9/2004 |

OTHER PUBLICATIONS

Zeiss, H.-J. "Enantioselective Synthesis of Both Enantiomers of Phosphinothricin via Asymmetric Hydrogenation of α-Acylamido Acrylates" *J. Org. Chem.*, vol. 56, pp. 1783-1788, 1991.
Weissermel et al., "Advances in Organophsphorus Chemistry Based on Dichloro(methyl)phosphane" *Angew. Chem. Int. Ed. Engl.*, vol. 20, pp. 223-233, 1981.
Zu. Obshch. Khim. vol. 46, pp. 243-246, 1977.
Gazizov et al., Zh. Obshch. Khim. (J. General Chemistry of the USSR), vol. 42, pp. 1718-1721, 1972.
English language Abstract of EP 0121226, corresponding to JP 59-184196, 1984.
English language Abstract of DE 19919848, corresponding to JP 2003-528572, 2003.
U.S. Appl. No. 12/529,953 to Kurihara et al., entitled "Process for Producing Phosphorus-Containing Dehydroamino Acid" which application is the National Stage of PCT/JP2008/055032, filed Mar. 19, 2008.
International Search Report for PCT/JP2008/055206, mailed Apr. 15, 2008.
International Preliminary Report on Patentability for PCT/JP2008/055206, issued Sep. 29, 2009.

*Primary Examiner* — Peter O Sullivan
(74) *Attorney, Agent, or Firm* — Greenblum & Bernstein, P.L.C.

(57) ABSTRACT

A method for efficiently producing 4-(hydroxymethylphosphinyl)-2-oxobutanoic acid, useful as a production intermediate of herbicide L-AMPB. The method comprises using a compound represented by the below formula (4): (4) where $R^1$ represents a $C_{1-4}$ alkyl group, arylmethyl group, or substituted arylmethyl group.

(4)

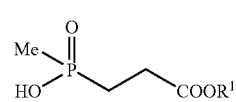

5 Claims, No Drawings

METHOD FOR PRODUCING PHOSPHORUS-CONTAINING α-KETO ACID

RELATED APPLICATION

The present application is an application claiming the priority based on Japanese patent application no. 2007-76541, filed on Mar. 23, 2007, and the entire disclosure of said Japanese patent application is incorporated herein by reference thereto.

FIELD OF THE INVENTION

The present invention relates to a method for producing 4-(hydroxymethylphosphinyl)-2-oxobutanoic acid which is useful as a production intermediate of a herbicide; L-2-amino-4-(hydroxymethylphosphinyl)-butanoic acid (in the below, it is abbreviated as L-AMPB).

BACKGROUND ART

It has been hitherto known that 4-(hydroxymethylphosphinyl)-oxobutanoic acid is an useful production intermediate of L-AMPB having herbicidal activity (see patent documents 1, 2 and 3; and non-patent document 1).

Also, it is only known as a method for synthesizing 4-(hydroxymethylphosphinyl)-oxobutanoic acid that 3-(alkoxymethylphosphinyl)-propionic acid ester (-propionate) or 3-(hydroxymethylphosphinyl)-propionic acid ester and oxalic acid diester are subjected to condensation reaction, then subjected to hydrolysis and decarboxylation (see patent document 4). In addition, it is known as a method for synthesizing 3-(hydroxymethylphosphinyl)-propionic acid ester that methylphosphinic acid is subjected to an addition reaction with acrylic acid ester (acrylate) (see patent document 5 and non-patent document 2). On the other hand, 3-(alkoxymethylphosphinyl)-propionic acid ester is synthesized such that methyldichlorophosphine is subjected to an addition reaction with acrylic acid, then the produced acid chloride is subjected to a reaction with alcohol (see non-patent documents 3 and 4).
Patent document 1: JP Kokai Publication H01-27485A
Patent document 2: JP Kohyo Publication 2003-528572A
Patent document 3: JP Kokai Publication S59-184196A
Patent document 4: JP Kokai Publication S56-92897A
Patent document 5: JP Kokai Publication H05-247068A
Non-Patent document 1: J. Org. Chem., 56, 1783-1788 (1991)
Non-Patent document 2: Angw. Chem. Int. Ed. Engl., 20, 223 (1981)
Non-Patent document 3: Zh. Obshch. Khim., 42, 1730(1972)
Non-Patent document 4: Zh. Obshch. Khim., 37, 710 (1967)

SUMMARY

The following analysis is given by the present invention. The above patent documents 1-5 and non-patent documents 1-4 are incorporated herein by references thereto.

However, the production yield of 4-(hydroxymethylphosphinyl)-2-oxobutanoic acid is as low as about 40% in the synthesizing method of the patent document 4 using 3-(hydroxymethylphosphinyl)-propionate ester.

In addition, in the methods of patent document 5 and non-patent document 2, there is a problem that methylphosphinic acid is hard to be prepared and the preparation is expensive.

Furthermore, in the methods of non-patent documents 3 and 4, there are problems such that the addition reaction is a reaction under high temperature and high pressure, so that byproduct such as chlorine gas is produced, which makes its procedural work difficult; and the preparation of methyldichlorophosphine is difficult and expensive.

It is an object of the present invention to provide a method for producing 4-(hydroxymethylphosphinyl)-2-oxobutanoic acid, which is a production intermediate of L-AMPB which is useful as a herbicide, efficiently.

As a result of considering the reaction of 3-(hydroxymethylphosphinyl)-propionic acid ester (-propionate) and oxalic acid diester in detail, the present inventors found that 4-(hydroxymethylphosphinyl)-2-oxobutanoic acid can be obtained with improved yield by performing the reaction in a range of reaction temperature between 40-60° C. within a range of 2-3 equivalents of a used amount of a base followed by acid hydrolysis and decarboxylation. Further, it was found that 3-(hydroxymethylphosphinyl)-propionic acid ester as a raw material can be produced efficiently from 3-(hydroxymethylphosphinyl)-propionic acid ester which is inexpensive, thereby the present invention has been accomplished.

That is to say, the present invention is as follows.

In a first aspect of the present invention, there is provided a method for producing a compound which is important as a precursor compound and represented by the following formula (6),

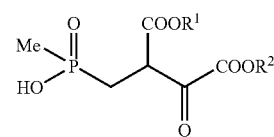

(6)

[in the formula, $R^1$ representing $C_{1-4}$ alkyl group, arylmethyl group, or substituted arylmethyl group; $R^2$ represents $C_{1-4}$ alkyl group, arylmethyl group, or substituted arylmethyl group];

wherein a compound represented by the following formula (4) is reacted with a compound represented by the following formula (5) under the existence of a base of 2-3 equivalents based on the compound of formula (4).

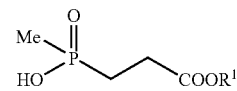

(4)

[in the formula, $R^1$ representing the same meaning as aforementioned]

 (5)

[in the formula, $R^2$ representing the same meaning as aforementioned].

And, in a second aspect of the present invention, there is provided a method for producing a compound of formula (6), as a step for producing the compound of formula (4), comprising:

a step that a compound represented by the following formula (1) is reacted with a compound represented by the following formula (2) under the existence of an acid or the existence of a condensation agent and a base,

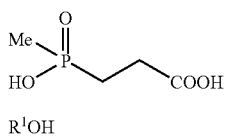

(1)

R¹OH   (2)

[in the formula, R¹ representing the same meaning as defined in the aforementioned formula (6)].

Further, in a third aspect of the present invention, there is provided a method for producing a compound of formula (6), as a step for producing the compound of formula (4), comprising:

a step that the compound of the formula (1) is reacted with a compound represented by the following formula (3) under the existence of a base,

R¹X   (3)

[in the formula, R¹ representing the same meaning as defined in the aforementioned formula (6) and X represents halogen atom].

Also, in a forth aspect of the present invention, there is provided a method for producing a compound of formula (6), as a step for producing the compound of the formula (4), comprising a step that the compound of the formula (1) is reacted with isobutylene under the existence of an acid catalyst.

Further, in a fifth aspect of the present invention, there is provided a method for producing a compound represented by the following formula (7),

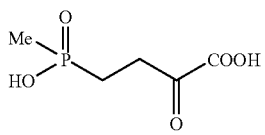

(7)

said method further including a step that wherein compound of formula (6) is hydrolyzed under the existence of an acid and subjected to decarboxylation.

Further, in a sixth aspect of the present invention, there is provided a method for producing a compound represented by the following formula (7),

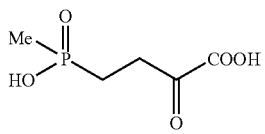

(7)

said method comprising:
(a) a compound represented by the following formula (1)

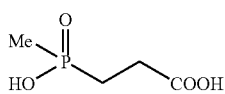

(1)

is reacted with a compound represented by the following formula (2)

R¹OH   (2)

[in the formula, R¹ representing $C_{1-4}$ alkyl group, arylmethyl group, or substituted arylmethyl group] under the existence of an acid or the existence of a condensation agent and a base; or the compound of the formula (1) is reacted with a compound represented by the following formula (3) under the existence of a base

R¹X   (3)

[in the formula, R¹ representing the same meaning as aforementioned, and X represents halogen atom]; or the compound of the formula (1) is reacted with isobutylene under the existence of an acid catalyst; to produce a compound represented by the following formula (4),

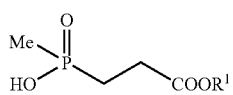

(4)

[in the formula, R¹ representing the same meaning as aforementioned], thereafter, (b) the compound of formula (4) is reacted with a compound represented by the following formula (5) under the existence of a base of 2-3 equivalents based on the compound of formula (4) to produce a compound represented by the following formula (6), further, $(COOR^2)_2$   (5)

[in the formula, R² representing $C_{1-4}$ alkyl group, arylmethyl group, or substituted arylmethyl group]

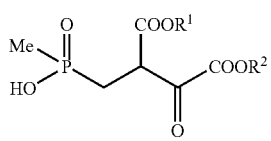

(6)

[in the formula, R¹ and R² representing the same meaning as aforementioned], and further (c) the compound of formula (6) is hydrolyzed under the existence of an acid and subjected to decarboxylation.

The precursor compound on the process for synthesizing 4-(hydroxymethylphosphinyl)-2-oxobutanoic acid which is a production intermediate of L-AMPB, which is useful as the herbicide, can be produced due to the producing method of the present invention. The producing method of the present invention is superior to the conventional method in a low-cost and efficiency. Therefore, the present invention is extremely industrially useful, especially in the field of pharmaceuticals needed for herbicidal action.

PREFERRED MODES

Groups shown as R¹ and R² for compounds represented by formulae (2)-(6) are explained.

$C_{1-4}$ alkyl groups shown as R¹ and R² mean straight chain or branched alkyl group having 1-4 carbons, in more detail, methyl group, ethyl group, n-propyl group, isopropyl group, n-butyl group, 2-butyl group, isobutyl group, t-butyl group and the like are listed.

As groups represented by $R^1$ and $R^2$ or aryl group on the groups represented by $R^1$ and $R^2$, phenyl group or naphthyl group and the like are listed.

The arylmethyl group represented by $R^1$ and $R^2$ means methyl group which is substituted by 1 to 3 aryl groups, in more detail, benzyl group, diphenylmethyl group, fluorenyl group, triphenylmethyl group and the like are listed.

The substituted arylmethyl group represented by $R^1$ and $R^2$ means that one or more hydrogen atom on benzene ring is substituted, preferably 1 to 3 hydrogen atoms are substituted; as a concrete substituted group(s), straight chain or branched $C_{1-4}$ alkyl group such as methyl group, ethyl group, n-propyl group, isopropyl group, n-butyl group, 2-butyl group, isobutyl group, t-butyl group and the like; halogen atom such as fluorine atom, chromium atom, bromine atom and the like; and $C_{1-4}$ alkoxy group such as methoxy group and the like; are listed.

Preferably, $R^1$ and $R^2$ are $C_{1-4}$ alkyl group, and more preferably methyl group and ethyl group.

The compound of formula (1) can be synthesized by the methods described in JP Kokai Publication 2004-345963A and JP Kokai Publication H05-247068A. (Disclosures of these documents are incorporated herein by references thereto.)

As concrete examples of the compounds represented by formula (2), ethanol, methanol, n-propanol, isopropyl alcohol, n-butanol, benzyl alcohol, and p-methylbenzyl alcohol are listed, and preferably, methanol.

As concrete examples of the compounds represented by formula (3), methyl iodide, ethyl iodide, n-propyl bromide, n-butyl bromide, benzyl bromide, benzyl chloride, and p-methylbenzyl bromide are listed, and more preferably, methyl iodide.

As concrete examples of the compounds represented by formula (4), are listed as follows:

3-(hydroxymethylphosphinyl)-propionic acid methyl ester,
3-(hydroxymethylphosphinyl)-propionic acid ethyl ester,
3-(hydroxymethylphosphinyl)-propionic acid n-propyl ester,
3-(hydroxymethylphosphinyl)-propionic acid n-butyl ester,
3-(hydroxymethylphosphinyl)-propionic acid t-butyl ester,
3-(hydroxymethylphosphinyl)-propionic acid benzyl ester, or
3-(hydroxymethylphosphinyl)-propionic acid p-methyl benzyl ester; and 3-(hydroxymethylphosphinyl)-propionic acid ethyl ester is preferable.

As concrete examples of the compounds represented by formula (5), oxalic acid dimethylester, oxalic acid diethylester, oxalic acid di n-propylester, oxalic acid n-butylester, oxalic acid dibenzylester or oxalic acid di p-methylbenzylester are listed, and oxalic acid dimethylester is preferable.

As concrete examples of the compounds represented by formula (6), compounds shown below are listed. In concrete examples, Ph represents phenyl group, Me represents methyl group, Et represents ethyl group, Pr represents propyl group and Bu represents butyl group.

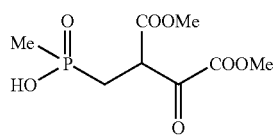

-continued

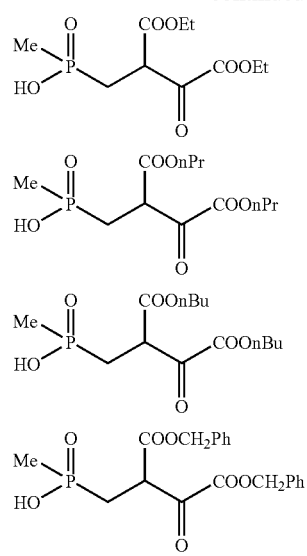

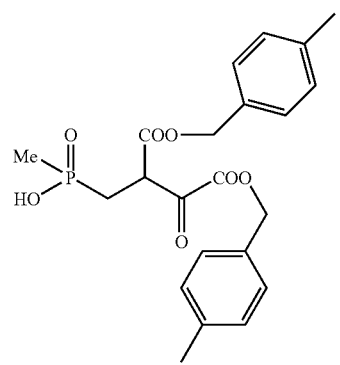

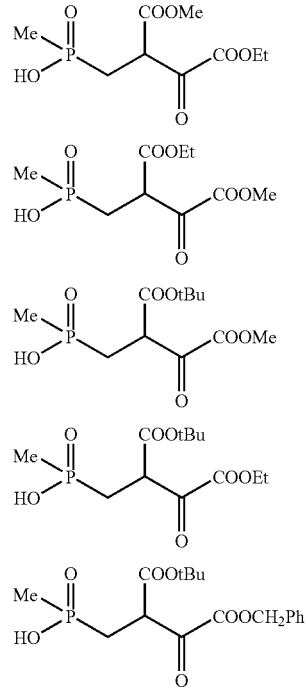

-continued

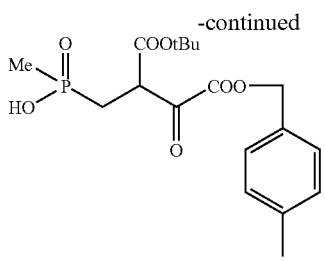

A compound shown below is preferable.

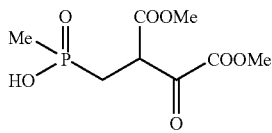

The compound of formula (6) has a relation of tautomer with a compound shown by the following formula (6'),

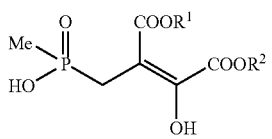

(6')

the compound of formula (6) and the compound of formula (6') are existing in equilibrium in a solution. Thereby, in the case where the compound of formula (6) is indicated, it is considered that the compound of formula (6) also includes the structure of the tautomer of the compound of formula (6').

As a solvent to be used in the producing method of the compound of formula (4) from the compound of formula (1) and the compound of formula (2) under existence of acid, halogenated hydrocarbon-based solvent such as methylene chloride and chloroform etc.; aromatic hydrocarbon-based solvents such as benzene and toluene etc.; alcohol solvent of formula (2); or mixed solvents including these two or more than two kinds of solvents described in the above are listed, and preferably, alcohol solvent of formula (2) and mixed solvent of formula (2) and benzene are listed. As an acid to be used, mineral acids such as hydrochloric acid, sulfuric acid and the like, aromatic sulfonic acids such as p-toluene sulfonic acid, benzene sulfonic acid and the like; and Lewis acids such as trifluoroborate etherate ($BF_3OEt_2$) are listed. The amount to be used of the acid is 0.01 to 0.3 equivalents based on the amount of the compound of formula (1). Preferably, the used amount of the compound shown by the formula (2) is 3 to 10 equivalents based on an amount of the compound of formula (1). The reaction temperature is 0 to 130° C., and preferably, the reaction is performed within a range of 20 and 90° C. The reaction time is generally 0.1-20 hours, and preferably, the reaction is performed within a range of 0.5 and 10 hours. In addition, the generated water is separated by azeotropic distillation using Dean-Stark water separating apparatus, if necessary.

After finish of the reaction, the reaction solution is concentrated or neutralized with alkali, then generated salt is removed. Thereafter, the compound of formula (4) can be isolated by concentrating the reaction solution. Usually, the reaction solution is used for the next step without the isolation.

In addition, the producing method of the compound of formula (4) from the compound of formula (1) and the compound of formula (2) under the existence of condensation agent and base is preferably applied to the case where the compound of formula (4) is manufactured from the compound of formula (2) in which $R^1$ is t-butyl group. Halogenated hydrocarbon-based solvent such as methylene chloride, chloroform etc.; aromatic hydrocarbon-based solvents such as benzene, toluene etc.; ether based solvents such as tetrahydrofuran, dimethoxyethane, dioxane etc.; ester based solvent such as ethyl acetate etc.; aprotic polar organic solvents such as N,N-dimethyl formamide dimethyl sulfoxide etc. are listed as solvents used in this method, and preferably, methylene chloride is listed. As condensation agents, carbodiimide based condensation agents such as dicyclohexyl carbodiimide, 1-ethyl-3-(3-(dimethylamino)propyl) carbodiimide hydrochloride etc. are listed, and dimethylaminopyridine is listed as a base. Preferably, the used amount of the compound shown by formula (2) is 1 to 2 equivalents based on the amount of the compound of formula (1). The reaction temperature is 0 to 130° C., and preferably, the reaction is performed within a range of 10 and 30° C. The reaction time is generally 1-20 hours, and preferably, the reaction is performed within a range of 3 and 12 hours.

Moreover, when the compound of formula (4) in which $R^1$ is t-butyl group is manufactured, it can be manufactured by reacting the compound of formula (1) and isobutylene under the existence of an acid catalyst. Halogenated hydrocarbon-based solvents such as methylene chloride, chloroform etc.;, aromatic hydrocarbon-based solvents such as benzene, toluene, etc.; ether based solvents such as dimethoxyethane and dioxane are listed as solvents used in this reaction, and preferably, methylene chloride is listed. As the acid catalyst to be used, concentrated sulfuric acid is listed. Isobutylene is used in an excess amount based on the amount of the compound of formula (1). The used amount of the acid is 0.05 to 0.2 equivalents based on the amount of the compound of formula (1). The reaction temperature is 0 to 50° C., and preferably, the reaction is performed within a range of 20 and 30° C. The reaction time is usually within a range of 1-48 hours, and preferably, the reaction is performed within a range of 12 and 24 hours.

As solvents used in the producing method of compound of formula (4) from the compound of formula (1) and the compound of formula (3) under existence of the base, halogenated hydrocarbon-based solvent such as methylene chloride, chloroform etc.; aromatic hydrocarbon-based solvents such as benzene, toluene etc.; ether based solvents such as tetrahydrofuran, dimethoxyethane, dioxane etc.; ketone based solvents such as acetone etc.; aprotic polar organic solvents such as N,N-dimethyl formamide and dimethyl sulfoxide; or alkanol solvents having 1-4 carbons such as methanol etc. are listed, and preferably, acetone, tetrahydrofuran, N,N-dimethyl formamide and dimethyl sulfoxide are listed. As bases to be used, sodium hydroxide, potassium hydroxide, sodium carbonate, potassium carbonate, sodium bicarbonate, cesium carbonate, triethylamine and diisopropylethylamine etc. are listed, and preferably, sodium hydrocarbonate is listed. The used amount of the base is 2 to 2.2 equivalents based on the amount of the compound of formula (1). Preferably, the used amount of the compound shown by the formula (3) is 1 to 1.2 equivalents based on the amount of the compound of formula (1). The reaction temperature is 0 to 100° C., and preferably, the reaction is performed within a range of 0 and 30° C. The reaction time is usually within a range of 0.5-24 hours, and preferably, the reaction is performed within a range of 1 and 10 hours.

As solvents used in the producing method of compound of formula (6) from the compound of formula (4) and the compound of formula (5) under existence of the base, halogenated hydrocarbon-based solvents such as methylene chloride, chloroform etc.; aromatic hydrocarbon-based solvents such as benzene, toluene etc., ether based solvents such as tetrahydrofuran, dimethoxyethane, dioxane etc.; aprotic polar organic solvents such as N,N-dimethyl formamide, dimethyl sulfoxide etc.; or alkanol solvents having 1-4 carbons such as methanol etc. are listed, and preferably, toluene is listed. As bases to be used, sodium hydride, potassium hydride, sodium methoxide, sodium ethoxide, potassium t-butoxide etc. are listed, and preferably, sodium methoxide is listed. The used amount of the base is 2 to 3 equivalents based on the amount of the compound of formula (4). Preferably, the amount of use of the compound shown by formula (5) is 1 to 1.6 equivalents based on the amount of the compound of formula (4). The reaction temperature is 0 to 100° C., and preferably, the reaction is performed within a range of 40 and 60° C. The reaction time is usually 0.5-12 hours, and preferably, the reaction is performed within a range of 1 and 7 hours.

After finish of the reaction, the reaction solution is vacuum concentrated after neutralization of the base with diluted hydrochloric acid, and the compound of formula (6) can be isolated by purifying silica gel chromatography. After obtaining crude product by distilling away the reaction solvent; usually, the reaction solution is used for the next step without isolation.

In a process in which a compound (7) is manufactured from the compound of formula (6), hydrochloric acid and sulfuric acid are listed as acids used, and water is listed as a solvent. Usually, the concentration of acid is in a range of 6-12 N within the case where hydrochloric acid is used and in a range of 2-18 N in the case where sulfuric acid is used. The reaction temperature is within a range of 20 to 150° C., and preferably, within a range of 50 to 120° C. The reaction time is within a range of 2 to 12 hours, and preferably, in a range of 4 to 8 hours.

The compound (7) can be isolated and purified using an ion exchange resin (BIO-RAD (registered TRADEMARK) Ag 1×2, eluent: 1% trifluoro acetate aqueous solution), for example.

4-(hydroxymethylphosphinyl)-2-oxobutanoic acid which is obtainable by the present invention can be converted to L-AMPB according to methods described in JP Kokai Publication H01-027485A, JP Kohyo Publication 2003-528572A, JP Kokai Publication S62-226993A and the like. (Disclosures of these documents are incorporated herein by reference thereto.)

EXAMPLES

The present invention is further described with reference to the following examples, which are not intended to restrict the present invention. In the examples, 3-(hydroxymethylphosphinyl)-propionic acid is used as a synthesized product according to the method described in JP Kokai Publication 2004-345963A.

Example 1

Manufacturing of methyl 3-(hydroxy)(methyl)phosphinyl) propionate

Thionyl chloride (500 mg) was added to methanol (4 ml) which was cooled at −10° C. and the solution was stirred for minutes, then 3-(hydroxymethylphosphinyl)-propionic acid (212 mg) was added to the solution and the resultant mixture was stirred for 18 hours. The reaction solution was subjected to vacuum concentration, thereby the subject compound (206 mg) (89% yield) was obtained.

$^1$H-NMR (CDCl$_3$) δ: 1.36 (3H, d, J=14.1 Hz), 1.95 (2H, dt, J=14.1, 8.1 Hz), 2.45-2.52 (2H, m), 3.55 (3H, s).

FABMASS: m/z 167 [M+H]$^+$.

Example 2

Manufacturing of methyl 3-(hydroxy)(methyl)phosphinyl) propionate

Concentrated sulfuric acid (18 mg) was added to a solution obtained by dissolving 3-(hydroxymethylphosphinyl)-propionic acid (212 mg) in methanol (4 ml), and the resultant solution was stirred for 18 hours at room temperature. Sodium bicarbonate (31 mg) was added to the resultant solution to obtain a reactant solution which was subjected to the vacuum concentration. Acetone was added to the residue; then after filtration of salt; the filtrate was subjected to vacuum concentration, to obtain the subject compound (208 mg) (90% yield).

$^1$H-NMR (CDCl$_3$) δ: 1.36 (3H, d, J=14.1 Hz), 1.95 (2H, dt, J=14.1, 8.0 Hz), 2.45-2.52 (2H, m), 3.55 (3H, s).

FABMASS: m/z 167 [M+H]$^+$.

Example 3

Manufacturing of methyl 4-(hydroxy)(methyl)phosphinyl)-3-(methoxycarbonyl)-2-oxobutanoate A solution obtained by dissolving dimethyl oxalate (850 mg) in toluene (2 ml) was added to a mixed solution of 28% sodium methoxide (2.89 g) and toluene (3 ml) under ice-cold condition. After stirring for 10 minutes under ice-cold condition, a solution obtained by dissolving methyl 3-(hydroxy)(methyl)phosphinyl) propionate (996 mg) was dissolved in toluene (1 ml) was added. After stirring for 10 minutes under ice-cold condition, the resultant solution was heated to 50° C. and stirred for 5 hours. 5 N hydrochloric acid was added to the reactant solution under ice-cold condition and adjusted to pH3, thereafter the solvent was distilled away under reduced pressure. The obtained residue was purified with silica gel chromatography (chloroform:methanol=10:1~chloroform:methanol:acetic acid=2:1:0.1), to obtain the subject compound (1.02 g) (68% yield).

$^1$H-NMR (CDCl$_3$) keto form δ: 1.36 (3H, d, J=14.0 Hz), 2.19-2.26 (1H, m), 2.34 (1H, td, J=14.3, 8.5 Hz) 3.72 (3H, s), 3.89 (3H, s), 4.53 (1H, ddd, J=11.5, 8.5, 6.0 Hz); enolform δ: 1.33 (3H, d, J=14.0 Hz), 3.17 (2H, d, J=17.0 Hz), 3.86 (3H, s), 3.88 (3H, s). The ratio of keto form to enolform was about 1:1.7.

APIMASS: m/z 253 [M+H]$^+$

Example 4

Manufacturing of 4-(hydroxy)(methyl)phosphinyl)-2-oxobutanoic acid

After dimethyl oxalate (850 mg) and methyl 3-(hydroxy)(methyl)phosphinyl) propionate (996 mg) was reacted in the same reaction condition as in Example 3, 5N hydrochloric acid was added to the reactant solution under ice-cold condition and adjusted to pH1, followed by distilling away the solvent under reduced pressure. Concentrated hydrochloric acid (6 ml) was added to the obtained residue and a stirring was performed for 6 hours at 100° C. After the reactant solution was subjected to vacuum concentration, the obtained residue was purified with BIO-RAD Ag1×2 (1% trifluoroacetic acid solution), to obtain, the subject compound (869 mg) (81% yield).

$^1$H-NMR (DMSO-$d_6$) δ: 1.30 (3H, d, J=14.2 Hz), 1.78 (2H, dt, J=14.2, 7.8 Hz), 2.98 (2H, dt, J=10.2, 7.8 Hz).

LCMASS: m/z 181 [M+H]$^+$.

It should be also understood that the foregoing disclosure based on examples however the present invention is not limited to the aforementioned examples. Further, changes and modifications of the modes and the examples are possible based on the essential technical concept within the entire disclosure of the invention (including claims). Various combinations, substitutions or selections of various disclosed constitutional elements or features may be made within the scope of claims. Patent and non-patent documents which are referred to or quoted in the present Description are incorporated in the present Description by reference thereto.

The invention claimed is:

1. A method for producing a compound represented by the following formula (6),

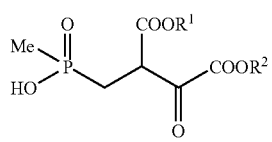

(6)

[wherein, $R^1$ represents $C_{1-4}$ alkyl group, arylmethyl group, or substituted arylmethyl group; $R^2$ represents $C_{1-4}$ alkyl group, arylmethyl group, or substituted arylmethyl group];

wherein a compound represented by the following formula (4) is reacted with a compound represented by the following formula (5) under the existence of a base of 2-3 equivalents based on the compound of formula (4),

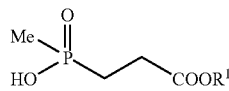

(4)

[wherein, $R^1$ represents the same meaning as aforementioned]

(COOR$^2$)$_2$ (5)

[wherein, $R^2$ represents the same meaning as aforementioned].

2. The method according to claim 1, wherein a reaction temperature is 40-60° C.

3. The method according to claim 1, wherein a step for producing the compound of formula (4) set forth in claim 1 comprises:

a step in which a compound represented by the following formula (1) is reacted with a compound represented by the following formula (2) under the existence of an acid or the existence of a condensation agent and a base;

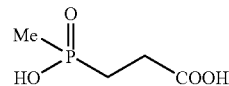

(1)

$R^1$OH (2)

[wherein, $R^1$ represents the same meaning as set forth in formula (6) in claim 1]; or a step in which the compound of formula (1) is reacted with a compound represented by the following formula (3) under the existence of a base;

$R^1$X (3)

[wherein, $R^1$ represents the same meaning as set forth in formula (6) in claim 1, and X represents halogen atom]; or a step in which the compound of formula (1) is reacted with isobutylene under the existence of an acid catalyst.

4. A method for producing a compound represented by the following formula (7),

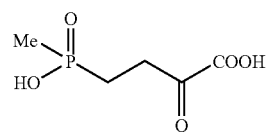

(7)

wherein said method further comprises a step in which the compound of formula (6) obtained by the method according to claim 1 is hydrolyzed under the existence of an acid to be subjected to decarboxylation.

5. A method for producing a compound represented by the following formula (7),

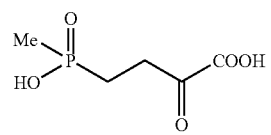

(7)

said method comprising:
(a) a compound represented by the following formula (1) is reacted with a compound represented by the following formula (2) under the existence of an acid or the existence of a condensation agent and a base

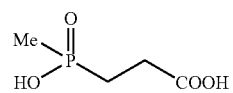

(1)

$R^1$OH (2)

[wherein, $R^1$ represents $C_{1-4}$ alkyl group, arylmethyl group, or substituted arylmethyl group]; or the compound of formula (1) is reacted with a compound represented by the following formula (3) under the existence of a base $R^1$X (3)

[wherein, $R^1$ represents the same meaning as aforementioned, and X represents halogen atom]; or the compound of the formula (1) is reacted with isobutylene under the existence of an acid catalyst;

to produce a compound represented by the following formula (4);

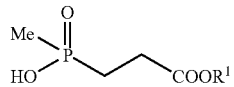
(4)

[wherein, $R^1$ represents the same meaning as aforementioned], thereafter, (b) the compound of formula (4) is reacted with a compound represented by the following formula (5) under the existence of a base of 2-3 equivalents based on the compound of formula (4);

$$(COOR^2)_2 \quad (5)$$

[wherein, $R^2$ represents $C_{1-4}$ alkyl group, arylmethyl group, or substituted arylmethyl group]

to produce a compound represented by the following formula (6);

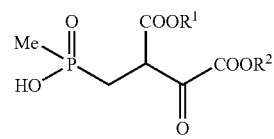
(6)

[wherein, $R^1$ and $R^2$ represent the same meaning as aforementioned]; and further, (c) the compound of formula (6) is hydrolyzed under the existence of an acid to be subjected to decarboxylation.

\* \* \* \* \*